(12) United States Patent
Meyer et al.

(10) Patent No.: US 7,909,771 B2
(45) Date of Patent: Mar. 22, 2011

(54) DIAGNOSIS OF SLEEP APNEA

(75) Inventors: Wolfgang Meyer, Erlangen (DE); Manuel Ebert, Erlangen (DE); Jochen Proff, Kalchreuth (DE)

(73) Assignee: Biotronik CRM Patent AG, Baar (CH)

( * ) Notice: Subject to any disclaimer, the term of this patent is extended or adjusted under 35 U.S.C. 154(b) by 935 days.

(21) Appl. No.: 11/771,026

(22) Filed: Jun. 29, 2007

(65) Prior Publication Data
US 2008/0051669 A1 Feb. 28, 2008

(30) Foreign Application Priority Data

Aug. 28, 2006 (DE) .......................... 10 2006 041 372
Mar. 3, 2007 (DE) .......................... 10 2007 010 353

(51) Int. Cl.
*A61B 5/0402* (2006.01)
(52) U.S. Cl. ........................................ 600/508; 600/509
(58) Field of Classification Search .................. 600/484, 600/509, 521, 510–519
See application file for complete search history.

(56) References Cited

U.S. PATENT DOCUMENTS

| | | | | |
|---|---|---|---|---|
| 5,299,119 A | * | 3/1994 | Kraf et al. ..................... | 600/509 |
| 6,416,473 B1 | * | 7/2002 | Risk et al. ..................... | 600/300 |
| 2003/0055348 A1 | * | 3/2003 | Chazal et al. ................. | 600/509 |
| 2005/0054940 A1 | * | 3/2005 | Almen ........................... | 600/509 |
| 2010/0292568 A1 | * | 11/2010 | Droitcour et al. ............. | 600/425 |

FOREIGN PATENT DOCUMENTS

| | | |
|---|---|---|
| EP | 1146433 | 10/2001 |
| WO | WO 2005/067790 | 7/2005 |

OTHER PUBLICATIONS

German Search Report, dated Oct. 18, 2007.

\* cited by examiner

*Primary Examiner* — Carl H Layno
*Assistant Examiner* — Gary A Porter, Jr.
(74) *Attorney, Agent, or Firm* — ARC IP Law, PC; Joseph J. Mayo

(57) ABSTRACT

Methods and apparatuses for detecting sleep apnea by analyzing characteristic physiological oscillations of the heart rate variability (HRV). Starting from recorded ECG data of the patient, for example, as a long-term sequence of the changing RR intervals, the heart rate variability is examined using autocorrelation calculations for the occurrence of rhythmic oscillations of various frequencies. If oscillations typical for apnea occur having very long period durations in the range of 20 to 80 seconds, these are detected as a maximum of the autocorrelation function. If a pathological sleep apnea accordingly exists, individual apnea events may be identified by prompt analysis of short recorded RR sequences, e.g., in the minute interval.

10 Claims, 6 Drawing Sheets

DIAGNOSIS OF SLEEP APNEA

This application takes priority from German Patent Application DE 10 2007 010 353.2 file 3 Mar. 2007 and German Patent Application DE 10 2006 041 372.5 filed 28 Aug. 2006, the specification of which is hereby incorporated herein by reference

BACKGROUND OF THE INVENTION

1. Field of the Invention

The present invention is in the field of medical measuring technology. In particular, the present invention relates to methods and apparatuses for detecting sleep apnea from cardiological data.

2. Description of the Related Art

Breathing pauses which last longer than 10 seconds are referred to as apnea. Breathing pauses of this type also sometimes occur in healthy people during sleep, this is physiologically normal sleeping behavior. In contrast, "sleep apnea syndrome" as a diagnosis is understood as the cyclic occurrence of respiratory arrest (of over 10 seconds duration) during the nocturnal sleeping phase having a repetition rate of more than 5 apneas per hour. The repetition rate is a measure of the degree of severity of the sleep apnea and is referred to as the apnea index. An apnea index of 5-10 corresponds to a light sleep apnea, 10-20 to a moderate sleep apnea, and more than 20 to a severe sleep apnea. A sleep apnea always results in significant health impairment (inter alia, heart rhythm interference, higher blood pressure, depression caused by sleep interruption), in some cases, death may even occur. It is estimated that approximately 3-5% of the adult population in the Western industrial nations are affected by sleep apnea. While the so-called obstructive form of sleep apnea occurs very frequently, particularly patients having congestive heart failure (CHF) are also affected by the central form (approximately 10% of all cases of sleep apnea, >30% in the event of CHF). However, mixed forms are also very common.

The occurrence and termination of a sleep apnea (obstructive or central) are characterized by a complex interplay of different factors. The normal sleeping state already differs in many ways from the waking state and in turn is composed of an array of different stages. These are differentiated primarily according to REM sleep (25%) and non-REM sleep (REM=rapid eye movement). Non-REM sleep is in turn composed of four different stages and all five classes are characterized, inter alia, by differing brain activity, which is expressed in various EEG patterns. An important special feature of REM sleep is atonia, which results in relaxation of the skeletal muscles.

The muscle atonia of REM sleep favors the occurrence of an obstruction, i.e., a temporary blockage of the airways, by relaxation of the pharyngeal muscles. If this occurs, the air is entirely or partially obstructed from flowing into the lungs in spite of existing respiratory movements. The direct result of this is a measurable reduction of the oxygen saturation of the blood. Selective chemoreceptors are stimulated by the drop of the oxygen saturation, which results in a nearly linear rise of the sympathicotonia over time. This continues for a period of time from at least 10 seconds to over 40 seconds. The increasing sympathetic activation results at its end in an activation of the brain activity up to leaving the sleep phase (which the patient usually no longer remembers in the morning). This results in a temporary removal of the obstruction, which may again occur after a period of time of 10 seconds to 40 seconds, however.

In the central form of sleep apnea, there is a breakdown of the control signals of the brain relevant for the breathing action, so that the respiratory movements do not occur at all. However, the result is also a cyclic cessation and resumption of the oxygen supply with a corresponding effect on the sympathicotonia.

The entire procedure during sleep apnea is thus not static, but rather comprises a dynamic oscillation. The cyclic activations occurring again and again are suspected to result in damage in the area of blood pressure regulation and the cardiac muscle, but are certainly disadvantageous because of their effect on the overall regulation by the autonomous nervous system. Important clinical symptoms of patients having sleep apnea are general sleepiness as well as a sympathicotonia elevated in relation to healthy people measurable via the muscular sympathetic nerve activity even in the waking state, this tonicity also not having the drop in the nocturnal phase which is typical in healthy people. The diurnal tonicity increase may also be confirmed in controlled experiments using analysis of the heart rate variability (HRV).

The standard method for diagnosing a sleep apnea comprises performing a polysomnographic examination in a suitable laboratory. For this purpose, there is long-term monitoring of the patient by an external Holter device, which is essentially based on measurement of the surface ECG and may optionally comprise further sensors, such as pulse oximetry probes.

This method has several disadvantages. Thus, it is certainly not stress-free for the patients, i.e., there are significant concerns in relation to acceptance and compliance in regard to long-term use of Holter devices by the patients. The analysis of the long-term measurements requires correspondingly high-performance data storage and processing and may only be automated to a restricted extent. Overall, the outlay required is significant, so that such examinations are costly. Long-term Holter examinations are therefore preferably first performed when there is already well-founded suspicion of apnea and obviously also may not be repeated at arbitrary intervals.

BRIEF DESCRIPTION OF THE INVENTION

The present invention is based on the method described for determining sleep apnea as the closest prior art. It is based on the object of developing a method and an assigned system for diagnosing sleep apnea, which requires significantly less effort and therefore is particularly also suitable for integration in cardiological implants and telemetry systems.

This object is fulfilled in a method according to the claims. Further advantages and special embodiments of the method according to the present invention are the subject matter of the dependent claims. The apparatus according to the present invention for performing the method in transportable or implanted devices in particular is also claimed.

The basis of the present invention is a special analysis of the instantaneous heartbeat rate. Changes occurring here are correlated to occurring apnea events and carry information about the pathological oscillations typical of apnea. The goal on one hand is the general diagnosis of whether apnea exists at all in the patient (having phases of more than 5 minutes per hour during nocturnal sleep), and, on the other hand (if apnea has been established), the prompt detection of occurring apnea events.

BRIEF DESCRIPTION OF THE DRAWINGS

The present invention is explained in greater detail in the following on the basis of preferred exemplary embodiments with reference to the drawings and the symbols and reference numerals used therein.

DETAILED DESCRIPTION OF THE INVENTION

Figure 1:
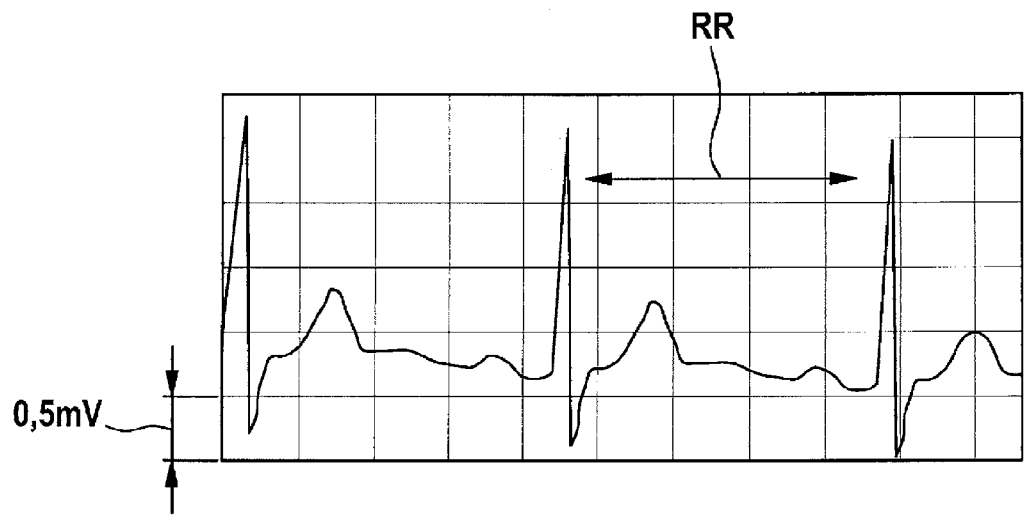
FIG. 1 shows a definition of the RR interval in ECG recordings.
Figure 2:
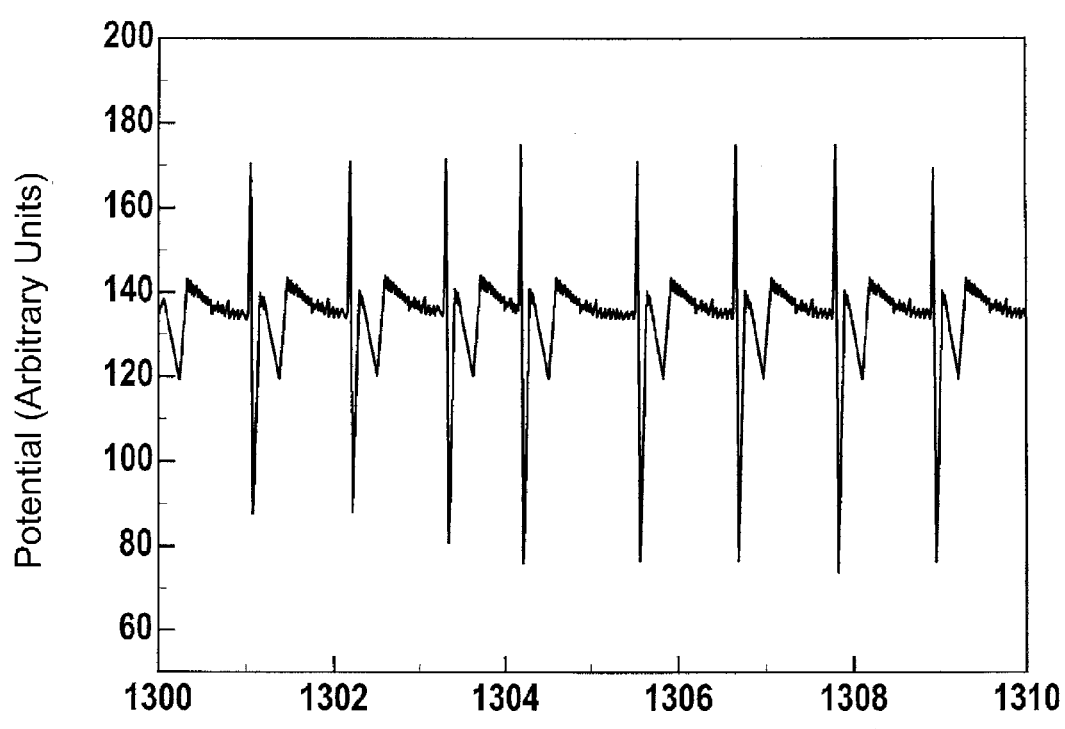
FIG. 2 shows an IEGM curve having intracardial R waves.

The heartbeat sequence is determined using a surface electrocardiogram (ECG) or from an intracardial electrogram (IEGM), which is measured using electrodes by an implant. The interval between two sequential heartbeats is generally defined via the so-called RR interval. This results as a chronological interval between two significant beats (so-called R waves) in the ECG or IEGM. These characteristic signals represent the contraction of the cardiac muscle in the course of the beat cycle. FIG. 1 shows a detail of a typical signal curve in a surface ECG having a marked RR interval. FIG. 2 shows the corresponding curve derived via intracardial electrodes.

Figure 3:
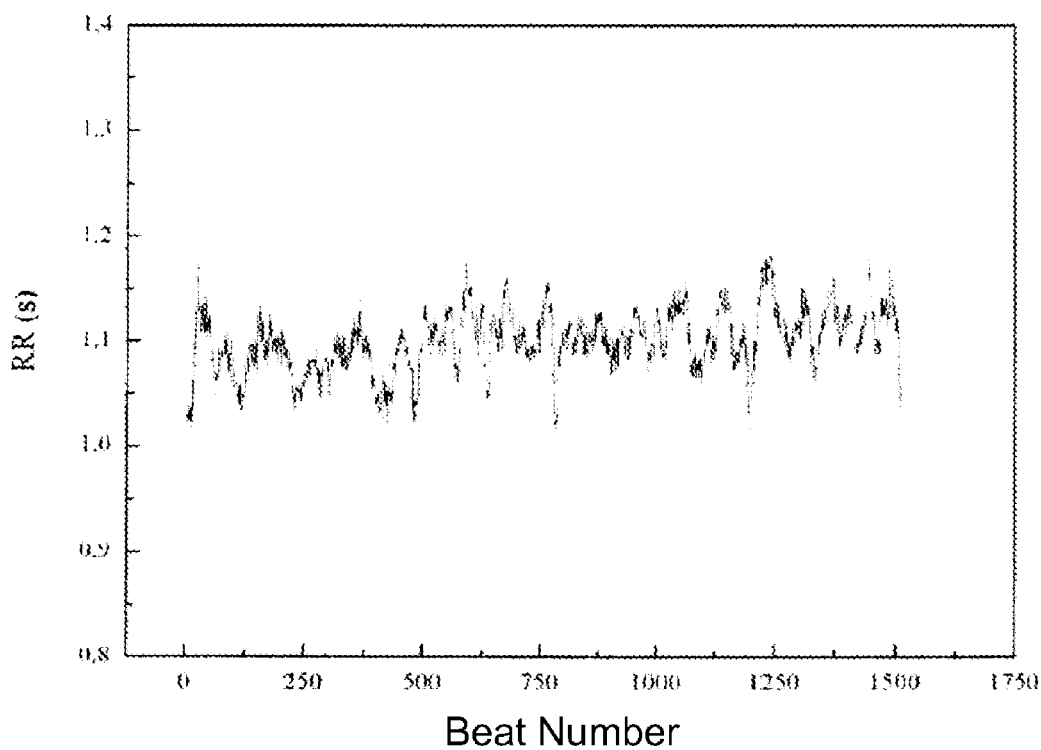
FIG. 3 shows fluctuations of the RR intervals.

A continuous measurement of R waves over a longer period of time provides a sequence of RR intervals which is referred to as a time array. A detail of such a time array is shown in FIG. 3. The heartbeat sequence does not show an equidistant sequence of R waves even in healthy people in the rest state, i.e., the interval lengths vary irregularly around a mean value (which is in turn a function of various external factors, such as patient age, "fitness", time of day, etc.).

For implants and in less complex external devices, e.g., transportable ECG measuring units carried by the patient, which may generally process smaller amounts of data than the complete ECG signal, the large quantities of recorded RR intervals occurring in long-term measurements are frequently too large for efficient data processing using the curves of the individual R waves resolved in morphological detail. The starting data for more extensive analysis are therefore frequently not the time arrays themselves, but rather the heart rate variability (HRV) as a chronological sequence of the occurring interval lengths. These data are shown in FIG. 3. The relatively small spontaneous fluctuations of the beat sequence having deviations of the interval duration of less than a tenth of a second around a mean chronological beat period of approximately 1.1 seconds are shown.

Figure 4:
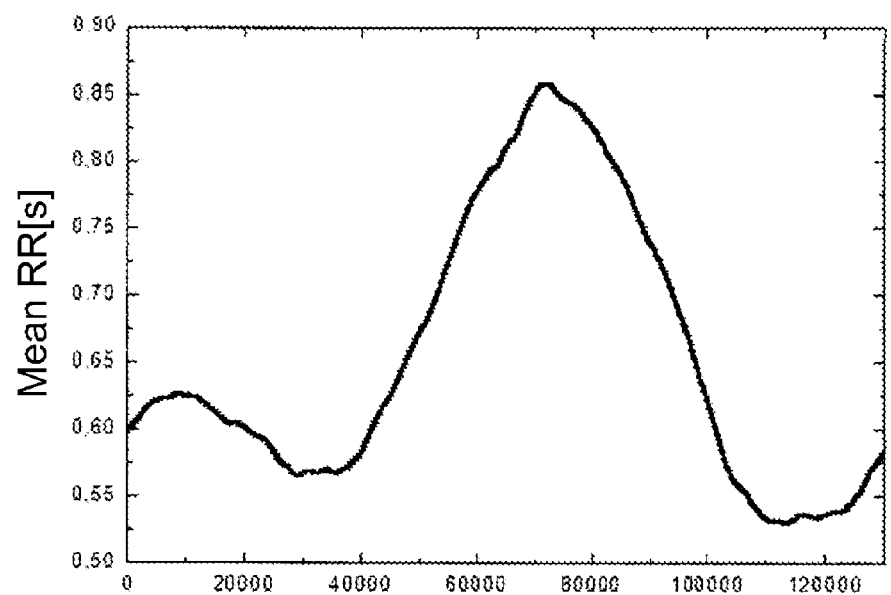
FIG. 4 shows circadian oscillations of the median heartbeat rate.

The mean beat period is known to be subjected to day/night oscillations, which are to be considered in an analysis of the HRV. FIG. 4 shows the change of the mean beat sequence of the patient over a 24-hour period of time. The HRV data range in the nocturnal phase is exclusively essential for detecting sleep apnea, the incorporation of the (much longer) diurnal phase would result in interference in the analysis in most cases due to concealment of the relevant information content.

Figure 5:
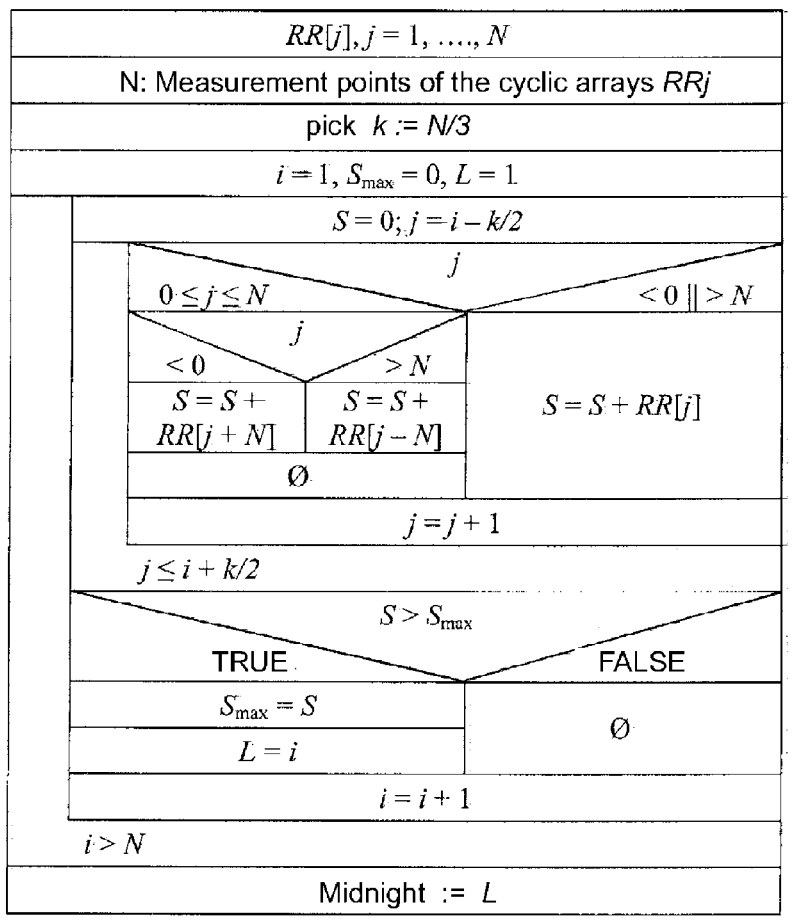
FIG. 5 shows a scheme for determining the nocturnal range from RR data.

Therefore, upon subsequent analysis of HRV data, the nocturnal range is preferably identified before further analysis. A simple example of a flowchart for establishing the nocturnal range is shown in FIG. 5. All of the data (data set from physionet.org) is divided into one-third nocturnal phase and two-thirds diurnal phase with the aid of the circadian variations in such a way that the middle of the nocturnal phase is assumed as the maximum of the mean RR interval over all combinations of ⅓ to ⅔. If the HRV data is instantaneously recorded, the nocturnal phases may also be logged by additional sensor data (e.g., impedance, activity, etc.). Therefore, before further analysis, the precise position of the nocturnal or sleeping phase may be established individually for the particular patient and measurement procedure.

The irregular oscillations of the RR intervals occurring in HRV data sets carry information about the regulation mechanisms of the cardiovascular system, so that they are used according to the present invention to detect differences between regular physiological behavior and pathological changes. The most important mechanisms used as a basis allow classification according to respiratory sinus arrhythmia, blood-pressure oscillations, thermoregulation, and renin-angiotensin system, which are influenced by vagotonia, sympathicotonia, and catecholamine level.

In the framework of a spectral HRV analysis, it is typical to define an array of frequency bands. The most important influencing factors may be coarsely assigned empirically to these bands:

The HF band (0.15 Hz-0.40 Hz) occurs due to vagally mediated (physiological) respiratory influences.

The LF band (0.04 Hz-0.15 Hz) is influenced both vagally and sympathetically and is linked to blood-pressure oscillations It is suspected of the typical VLF band (0.003 Hz-0.04 Hz) that its origin is partially physiologically caused by the renin-angiotensin-aldosterone system, but particularly requires a strong vagal mediation The basis for the diagnosis according to the present invention of a sleep apnea is the fact that the rhythmic fluctuations of the sympathicotonia having period durations between 20 and 80 seconds result in a correlated oscillation of the RR interval in a corresponding spectral range (usually used: 0.005 Hz to 0.03 Hz). This long-wave fluctuation is theoretically always expected to be pronounced in the event of complete apnea, because it is a necessary result of temporary respiratory arrest. It is to be assumed that the amplitude and frequency of the oscillation may vary individually by at least a factor of two, but this oscillation is so generally present that it represents the approach according to the present invention for a sensitive detection of apnea.

Known methods for an analysis of the long-wave oscillation component are wavelet transformation, Hilbert transformation, and Fourier transformation. However, the interpretation is difficult, because either a discriminator must be connected downstream, fixed limits must be predefined, or derived parameters having arbitrary limits must be used.

To overcome these difficulties, in the method according to the present invention, features of the spectral power density are detected in the time range using the autocorrelation function $$C(\tau) = \sum_{i=0}^{N-\tau} RR(i)RR(i+\tau)$$

N is the number of measured points, RR(i) is the standardized RR interval measured as the number i, and τ is a time shift, which the RR signal shifts in relation to itself. The variable τ passes through the range of integers from τ=0 up to a physiologically advisable upper limit of, for example τ=120 at step width Δτ. The step width Δτ does not necessarily have to be equal to one, but is selected in this way for the following description as a special case. Larger values of the step width reduce the computing effort.

The autocorrelation function has the essential property, in the event of a shift τ, which results in a relative congruence equality of the signal with itself, of having a maximum. In contrast, if the shift results in a mutual curve of shifted and unshifted signal, C(τ) assumes a minimum. The autocorrelation function is always maximum in the event of zero shift, i.e., identity.

Because the main identifier of apnea is the occurrence of long-wave oscillations of the RR interval in the time range between 20 and 120 beats, in the event of existing respiratory interference, a local maximum of C(τ) is expected in the event of shifts of τ in this range. Therefore, the sequence for apnea detection may be subdivided into the following steps:
determining the autocorrelation function,
rising search for the first minimum (e.g., from τ=3),
search for the position of the absolute maximum above the first minimum.

Figure 6:
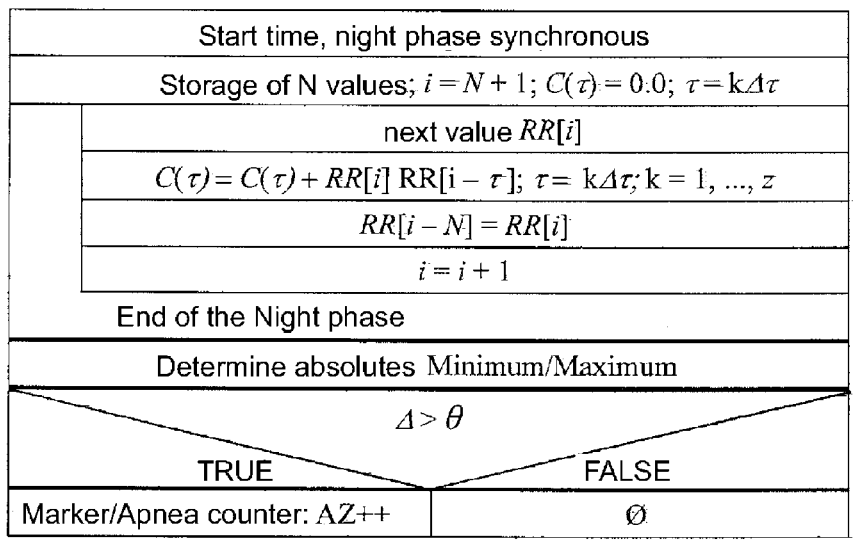
FIG. 6 shows a flowchart of the method according to the present invention for apnea recognition using autocorrelation function.

FIG. 6 shows a corresponding flowchart of the method according to the present invention, which may be used as an algorithm for automated apnea diagnosis. The criteria or threshold values used (identified in FIG. 6 as Δ and θ) for the position of first minimum and following maximum of the autocorrelation curve may be determined from general data (e.g., as empirical guidelines), or may be tailored individually to a patient, e.g., if this patient is not to be classified in the general pattern because of special physiology or clinical picture.

Figure 7:
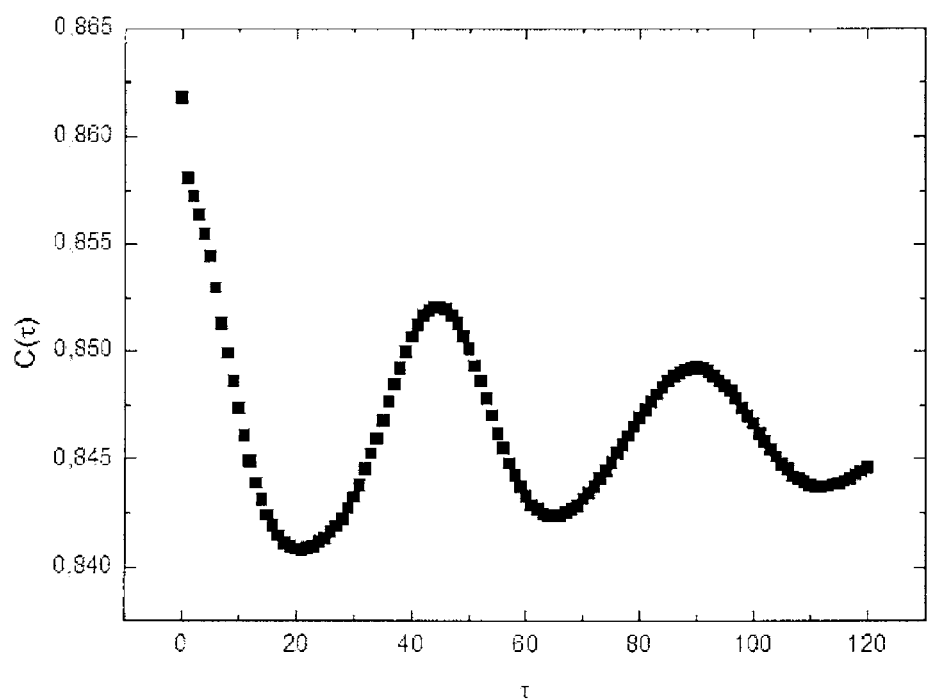
FIG. 7 shows an autocorrelation having a clear maximum in the apnea time range.

FIG. 7 shows an autocorrelation function thus obtained in the event of existing sleep apnea. The maximum is clearly pronounced at a long shift of τ=45. The large τ value of the position of the maximum provides the significant information about the presence of a sleep apnea here. The degree by which the maximum is pronounced may be used to evaluate the severity of the apnea.

In contrast, if the patient is free of apnea, the long-wave maximum is missing, in addition, a local maximum is to be expected during the oscillations of the blood-pressure variability (LF) or the respiratory sinus arrhythmia (HF). This results because the typical oscillations are undisturbed and, in addition, because the normal state is distinguished by a reduced sympathicotonia in relation to sleep apnea. These oscillations cause a maximum of the autocorrelation function at approximately τ<15.

Figure 8:
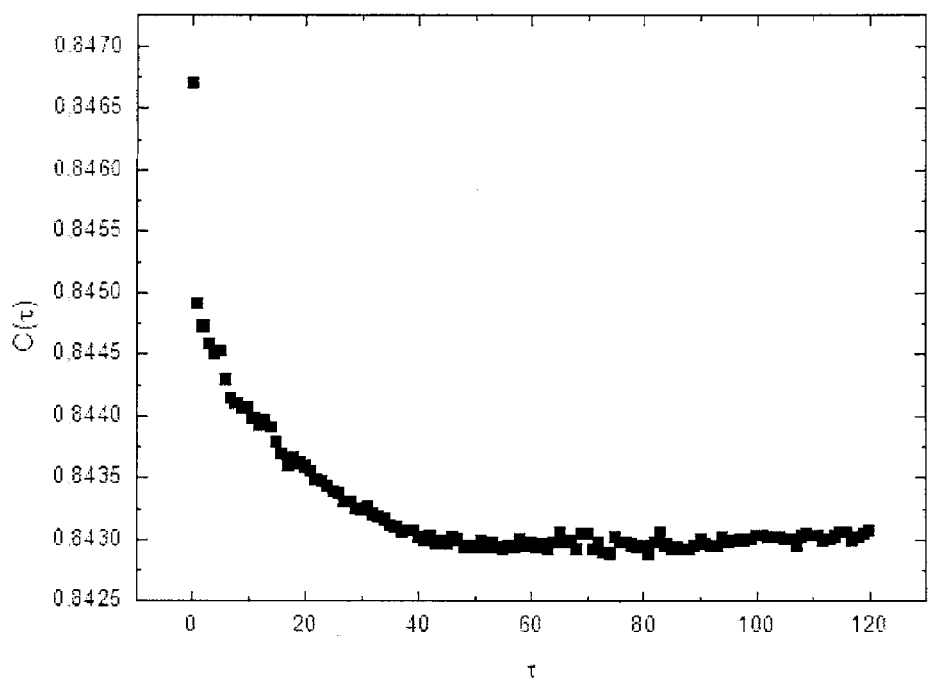
FIG. 8 shows an autocorrelation of a control dataset (apnea-free).
Figure 9:
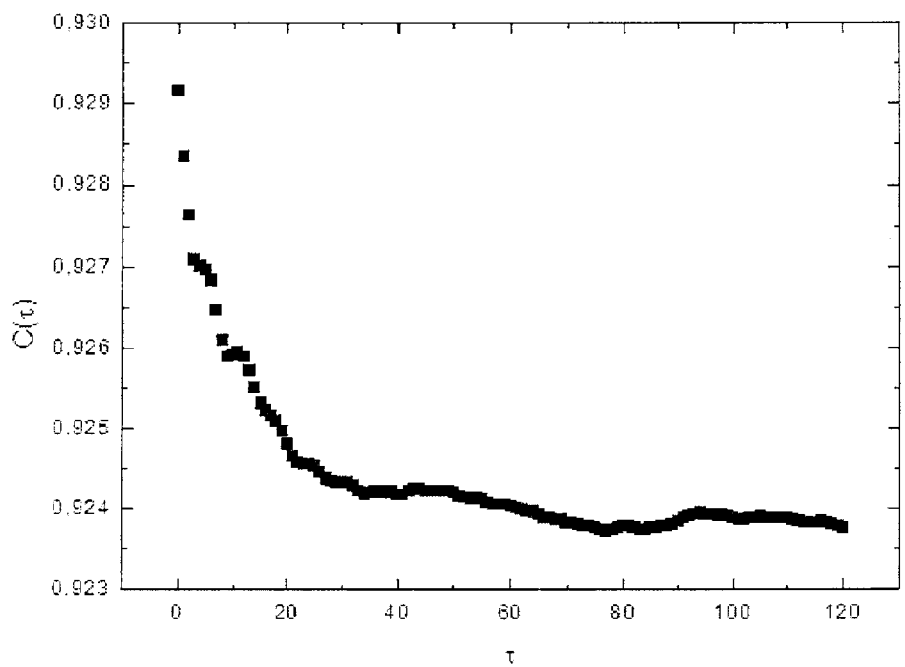
FIG. 9 shows an autocorrelation having weakly pronounced apnea maximum.

FIGS. 8 and 9 are examples of these conditions, ascertained from control data. In both cases, a maximum in the decisive range (τ=40 through 50) is not or is only very weakly implemented. Small deviations in the monotonously decreasing curve are recognizable in the area of physiological blood-pressure variability (LF) and respiratory variability (HF)

In an expanded embodiment of the method according to the present invention, the significance of the oscillations established using autocorrelation in the apnea range may be increased for delimitation in relation to other events having influence on the HRV: the apnea band is embedded in the VLF band and may also partially overlap with the LF band, so that a small or also moderate increase of the power density in the apnea band, inter alia, may also be attributed to other physiological phenomena. This may occur, for example, if a pronounced vagotonia exists, which significantly strengthens the VLF component. In such a case, however, the fluctuation of the RR intervals as a whole is significantly increased, which is not the case in the event of an apnea. Thus, in the event of a slight increase of the power density in the apnea band, if a significant increase of the HRV overall fluctuation is detected in parallel, for which methods are known, apnea is to be precluded as the sole cause.

Establishing an apnea using the suggested autocorrelation method has the essential advantage that a diagnosis may be performed solely from RR data using only one parameter (localization of a maximum in the apnea band). For this purpose, only very simple data processing operations (multiplication and summation of integers) are necessary. This requires only little data processing resources and may therefore also be managed by devices having restricted functional scope. These particularly also include implants (cardiac pacemakers, defibrillators, etc.) and wearable devices, which are integrated in a diagnostic telemetry system, for example.

If a sleep apnea has been established using autocorrelation methods, in an expanded embodiment of the method according to the present invention, the diagnostic procedure may be refined to direct detection of individual apnea events. For such prompt sensing in the minute range, it is necessary to already prepare an analysis from a relatively small data field (RR log of a few minutes), which is then performed cyclically, e.g., in a minute cycle. To be able to detect long-wave oscillations correctly on such a short time scale, a two-stage algorithm which is intentionally kept simple is used according to the present invention, because the data processing required for this purpose may also be performed using simple means. Firstly, components of higher frequency oscillations are removed from the signal. This may be performed using a sliding mean-value filter which requires particularly few computing operations, for example. If sufficient resources are present, higher performance filter operations (e.g., recursive mean-value filter) may also be used to improve the selectivity of the low-pass filter. The total energy of the remaining signal is then a measure of the presence of long-wave oscillations. This total energy is ascertained, for example, by summation of the absolute value differences of sequential RR intervals, according to $$S = \sum_{i=2}^{N} |RR(i) - RR(i-1)|$$

Figure 10:
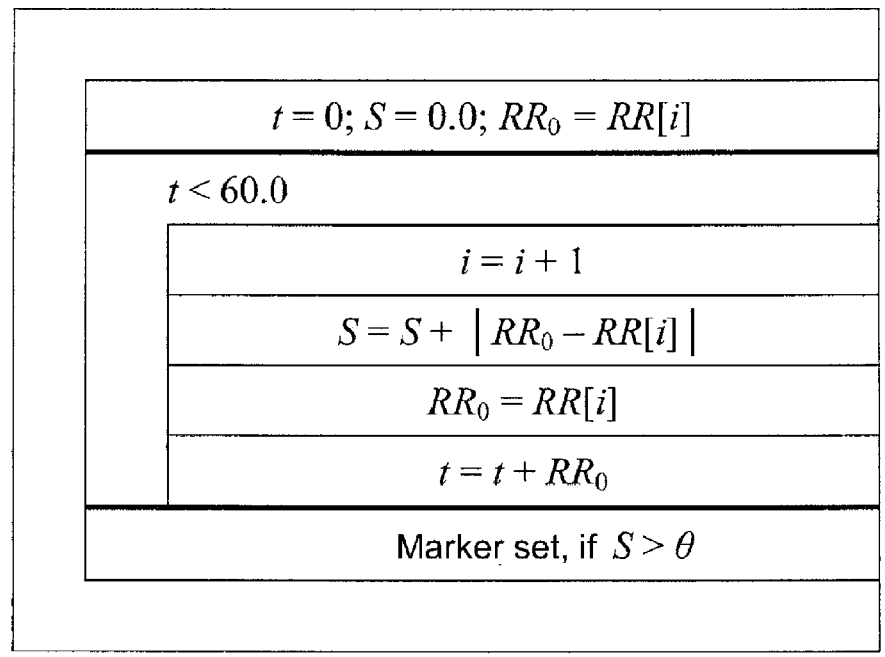
FIG. 10 shows a flowchart for prompt detection of individual apnea events.

N describing the number of intervals in the period of time of a minute, for example. If the summation value S thus obtained is above a predefined threshold θ, this is evaluated as a signal for a current apnea. FIG. 10 shows a flowchart.

The threshold value to be input previously may typically not be specified from general experiential values, but rather is a function of the individual data of the particular patient. Because previously the diagnosis of a sleep apnea has been performed using analysis of long-term HRV data (at least 24 hours), the patient-related base intervals of the heart rate and their circadian changes (compare FIG. 4) are known and may be used to establish the threshold value. For an apnea patient, the nocturnal phase is composed of minute intervals in which apnea exists and of intervals in which normal breathing occurs. Therefore, the distribution density function of the absolute value summation values is composed of two ranges which more or less overlap, the higher values of the absolute value sum S being assigned to the apnea intervals. For an automatic, objective, and effective establishment of a threshold value between apnea and normal intervals, for example, the entropy method already developed for extrasystolic filters suggests itself. Alternatively, other methods may also be used, which provide an automatically determinable threshold value at sufficient sensitivity and specificity on an empirical basis, e.g., the simple mean value of the distribution, the median of the distribution, or suitable other percentiles. The threshold value determination may be performed depending on the method, outlay and resources in the implant, after telemedical data transfer, or in the scope of aftercare.

Figure 11:
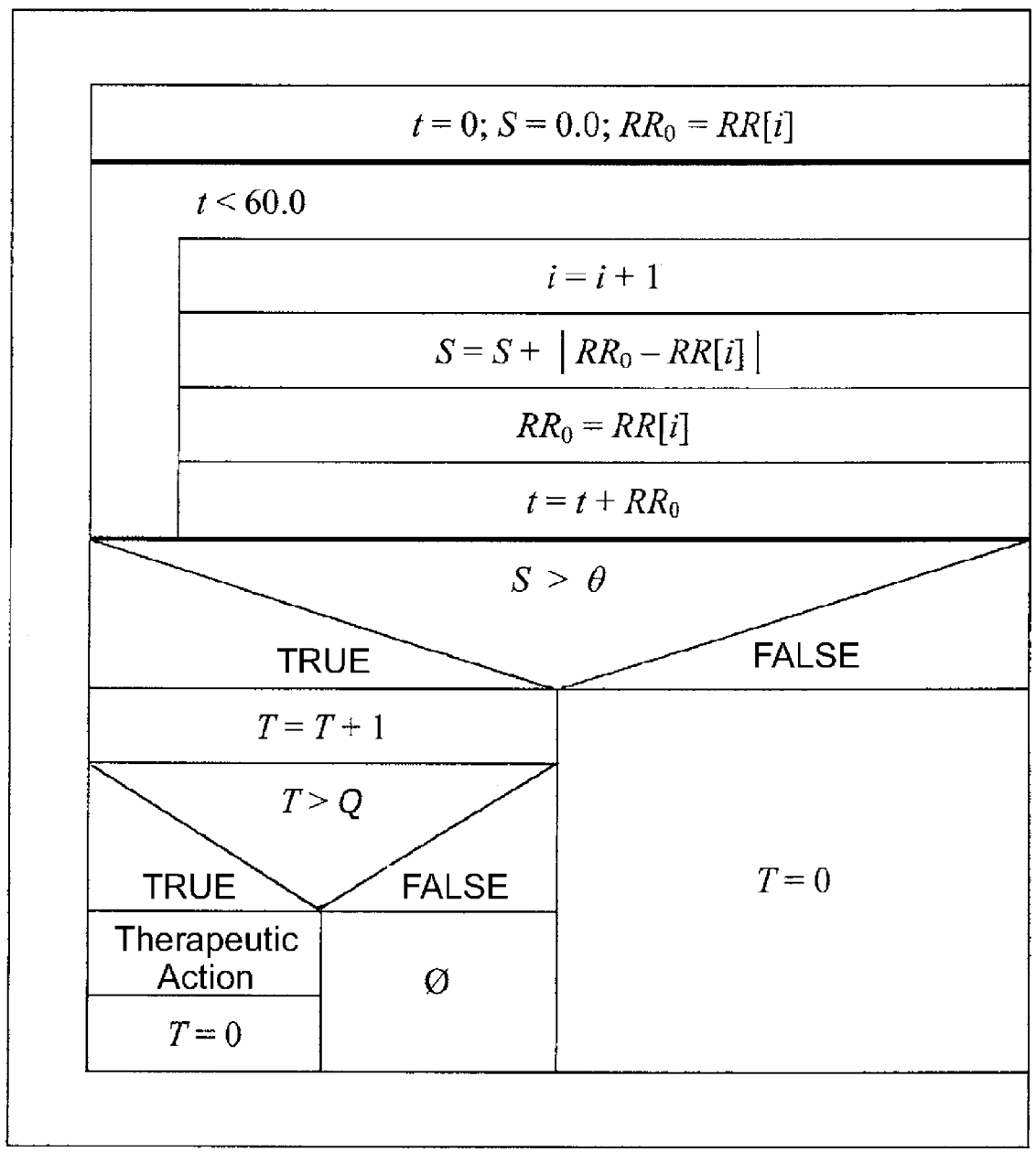
FIG. 11 shows a flowchart for prompt detection of individual apnea events.

The method may also be used to detect a current sequence of apnea events and thus to be able to engage with treatment immediately, for example. For this purpose, the analysis, as shown in FIG. 11 as a flowchart, may be supplemented by a further freely selectable threshold value Q, which predefines a critical number of apnea events. If more than Q apnea events are detected in sequence, a corresponding signal may be generated automatically.

The method presented here according to the present invention for diagnosing sleep apnea is particularly suitable for implementation in devices having restricted resources. It is particularly advantageous that the particular critical parameter may be adapted to the available technical resources. For example, the increment for the shift of the autocorrelation function may be increased, which causes a direct reduction of the processing outlay. Therefore, even in the event of restricted computing capacity, measurements may even be executed over multiple days and, in spite of fewer operations per cycle, a statistically relevant correlation statement may be generated.

The present invention allows the characterization of an apnea status and automatic recognition of changes which occur. For example, a rapid diagnostic opinion may be reached by telemetric transmission of little data. The amount of data to be externally transmitted is additionally very small and thus allows checking of the patient status without problems, e.g., in a 24-hour rhythm. Complex analysis of morphology criteria, which is susceptible to error, is dispensed with, because only the easily available RR interval is used.

An apparatus for implementing the method according to the present invention does not require any special effort, so that it is also suitable for wearable devices and particularly also for implants. The calculations to be performed for this purpose in an implant, for example, relate to a few simple numeric operations, the algorithm to be used for determining the autocorrelation function and the sum of the absolute value differences of sequential RR intervals is restricted to a calculation of interval values. The data storage in the implant requires few bytes. Functions of this type may already be performed by very simple data processing components. The energy consumption is correspondingly low.

In an expanded embodiment of the present invention, means for implementing the method according to the present invention are integrated as an algorithm on corresponding miniaturized data processing components in analysis devices, in particular implants, for example, as application-specific integrated circuits (ASICs) or microprocessors (μP). Therefore, the individual analysis sequences are also possible in the implants themselves. An existing apnea may then be detected by the implant itself and the corresponding information may be transmitted as a signal for further diagnosis.

In addition to the detection of sleep apnea, the improvement of continuous monitoring in the event of CHF is advantageous. The recognition of progressive or acute worsening of the CHF illness is the focus point, because progress of the illness may result in increased central sleep apnea, on the other hand, an existing sleep apnea may also have a negative effect on the CHF illness course.

What is claimed is:

1. A method for detecting sleep apnea from ECG data comprising:
   detecting heartbeats as a sequence of R waves using electrodes;
   using a data processing component or application-specific integrated circuit or microprocessor in
      recording variations of RR interval lengths occurring in said sequence of R waves as a heart rate variability in a heart rate variability log;
      analyzing said heart rate variability log for existing heart rate variability oscillations in a low-frequency range using an autocorrelation function $$C(\tau) = \sum_{i=0}^{N-\tau} RR(i)RR(i+\tau)$$

wherein N is a number of measured points, RR(i) is a standardized RR interval measured at index i, and τ is a time shift to shift RR in relation to itself at index i+τ, wherein τ passes through a range of integers from τ=0 up to a predefined upper limit;
   evaluating said heart rate variability oscillations for existing sleep apnea in a time range between 20 and 120 beats corresponding to said index i by
      searching for a first minimum after τ=3 and
      searching for a position of an absolute maximum above said first minimum.

2. The method according to claim 1, further comprising detecting frequency position and/or intensity of oscillations using said autocorrelation function to evaluate a severity of said sleep apnea.

3. The method according to claim 1, wherein said analyzing said heart rate variability log is restricted to analyzing data ranges of nocturnal and/or sleep phases.

4. The method according to claim 1, further comprising analyzing a quantity of scattering of a recorded heart rate variability to identify said sleep apnea and a severity of said sleep apnea.

5. The method according to claim 1, further comprising detecting individual apnea events by analyzing predefined time sections of said heart rate variability log for low frequency oscillations, using absolute value summation of interval differences $$S = \sum_{i=2}^{N} |RR(i) - RR(i-1)|$$

wherein N is a number of intervals and wherein a current apnea is determined if summation value S is above a predefined threshold.

6. A apparatus for detecting sleep apnea from ECG data comprising:
   electrodes configured to detect heartbeats as a sequence of R waves;
   a data processing component or application-specific integrated circuit or microprocessor configured to:
      record variations of RR interval lengths that occur in said sequence of R waves as a heart rate variability in a heart rate variability log;
      analyze said heart rate variability log for existing heart rate variability oscillations in a low-frequency range through use of an autocorrelation function $$C(\tau) = \sum_{i=0}^{N-\tau} RR(i)RR(i+\tau)$$

wherein N is a number of measured points, RR(i) is a standardized RR interval measured at index i, and $\tau$ is a time shift to shift RR in relation to itself at index i+$\tau$, wherein $\tau$ passes through a range of integers from $\tau$=0 up to a predefined upper limit;

evaluate said heart rate variability oscillations for existing sleep apnea in a time range between 20 and 120 beats that corresponds to said index i through a search for a first minimum after $\tau$=3 and a search for a position of an absolute maximum above said first minimum.

7. The method according to claim 6, wherein said data processing component or application-specific integrated circuit or microprocessor is further configured to detect frequency position and/or intensity of oscillations using said autocorrelation to evaluate a severity of said sleep apnea.

8. The method according to claim 6, wherein said data processing component or application-specific integrated circuit or microprocessor that is configured to analyze said heart rate variability log is restricted to analyze data ranges of nocturnal and/or sleep phases.

9. The method according to claim 6, wherein said data processing component or application-specific integrated circuit or microprocessor is further configured to analyze a quantity of scattering of a recorded heart rate variability to identify said sleep apnea and a severity of said sleep apnea.

10. The method according to claim 6, wherein said data processing component or application-specific integrated circuit or microprocessor is further configured to detect individual apnea events through analysis of predefined time sections of said heart rate variability log for low frequency oscillations, through absolute value summation of interval differences $$S = \sum_{i=2}^{N} |RR(i) - RR(i-1)|$$

wherein N is a number of intervals and wherein a current apnea is determined if summation value S is above a predefined threshold.

* * * * *